(12) United States Patent
Grenier et al.

(10) Patent No.: US 8,221,986 B2
(45) Date of Patent: *Jul. 17, 2012

(54) DIAGNOSTIC TEST FOR THE DETECTION OF A MOLECULE OR DRUG IN WHOLE BLOOD

(75) Inventors: Frank C. Grenier, Libertyville, IL (US); Ryan F. Workman, Gurnee, IL (US); Hina N. Syed, Gurnee, IL (US); Salman Ali, Hoffman Estates, IL (US)

(73) Assignee: Abbott Laboratories, Abbott Park, IL (US)

( * ) Notice: Subject to any disclaimer, the term of this patent is extended or adjusted under 35 U.S.C. 154(b) by 174 days.

This patent is subject to a terminal disclaimer.

(21) Appl. No.: 12/491,309

(22) Filed: Jun. 25, 2009

(65) Prior Publication Data

US 2009/0325193 A1    Dec. 31, 2009

Related U.S. Application Data

(63) Continuation of application No. PCT/US2007/088087, filed on Dec. 19, 2007.

(60) Provisional application No. 60/882,732, filed on Dec. 29, 2006.

(51) Int. Cl.
*G01N 33/53* (2006.01)

(52) U.S. Cl. .................................... 435/7.1; 436/518

(58) Field of Classification Search ........................ None
See application file for complete search history.

(56) References Cited

U.S. PATENT DOCUMENTS

| | | | |
|---|---|---|---|
| 4,624,930 A | 11/1986 | Tanswell et al. |
| 4,652,517 A | 3/1987 | Scholl et al. |
| 5,134,875 A | 8/1992 | Jensen et al. |
| 5,135,875 A | 8/1992 | Meucci et al. |
| 5,169,773 A | 12/1992 | Rosenthaler et al. |
| 5,217,971 A | 6/1993 | Takasugi et al. |
| 5,322,772 A | 6/1994 | Soldin |
| 5,350,574 A | 9/1994 | Erlanger et al. |
| 5,354,845 A | 10/1994 | Soldin |
| 5,489,668 A | 2/1996 | Morrison et al. |
| 5,498,597 A | 3/1996 | Burakoff et al. |
| 5,525,523 A | 6/1996 | Soldin |
| 5,650,228 A | 7/1997 | May |
| 5,650,288 A | 7/1997 | MacFarlane et al. |
| 5,698,448 A | 12/1997 | Soldin |
| 5,750,413 A | 5/1998 | Morrison et al. |
| 5,780,307 A | 7/1998 | Soldin |
| 5,897,990 A | 4/1999 | Baumann et al. |
| 5,955,108 A | 9/1999 | Sutton et al. |
| 5,990,150 A | 11/1999 | Matsui et al. |
| 6,054,303 A | 4/2000 | Davalian et al. |
| 6,087,134 A | 7/2000 | Saunders |
| 6,187,547 B1 | 2/2001 | Legay et al. |
| 6,197,588 B1 | 3/2001 | Gray et al. |
| 6,239,102 B1 | 5/2001 | Tiemessen |
| 6,328,970 B1 | 12/2001 | Molnar-Kimber et al. |
| 6,410,340 B1 | 6/2002 | Soldin |
| 6,541,612 B2 | 4/2003 | Molnar-Kimber et al. |
| 6,858,439 B1 | 2/2005 | Xu et al. |
| 6,913,580 B2 | 7/2005 | Stone |
| 6,998,246 B2 | 2/2006 | Schäffler et al. |
| 7,189,582 B2 | 3/2007 | Chen et al. |
| 2002/0002273 A1 | 1/2002 | Sedrani et al. |
| 2002/0022717 A1 | 2/2002 | Sedrani et al. |
| 2002/0055124 A1 | 5/2002 | Janda et al. |
| 2002/0151088 A1 | 10/2002 | Molnar-Kimber et al. |
| 2003/0157556 A1 | 8/2003 | Maggiore et al. |
| 2003/0235839 A1 | 12/2003 | McKernan et al. |
| 2004/0062793 A1 | 4/2004 | Van Dyke |
| 2004/0101429 A1 | 5/2004 | Ogawa |
| 2004/0102429 A1 | 5/2004 | Modak et al. |
| 2005/0033035 A1 | 2/2005 | Beisel et al. |
| 2005/0055126 A1 | 3/2005 | Genma et al. |
| 2005/0112778 A1 | 5/2005 | Wang et al. |
| 2005/0164323 A1 | 7/2005 | Chaudhary et al. |
| 2005/0272109 A1 | 12/2005 | Schaffler et al. |
| 2006/0003390 A1 | 1/2006 | Schaffler et al. |
| 2006/0020401 A1 | 1/2006 | Davis et al. |
| 2006/0062793 A1 | 3/2006 | Webb et al. |
| 2006/0216770 A1 | 9/2006 | Kasper et al. |
| 2006/0257957 A1 | 11/2006 | Drengler et al. |
| 2008/0020401 A1 | 1/2008 | Grenier et al. |
| 2008/0160499 A1 | 7/2008 | Grenier et al. |
| 2008/0176756 A1 | 7/2008 | Siegel et al. |
| 2009/0325197 A1 | 12/2009 | Drengler et al. |
| 2009/0325198 A1 | 12/2009 | Holets-McCormack |

FOREIGN PATENT DOCUMENTS

EP          0293892      12/1988
(Continued)

OTHER PUBLICATIONS

Alak et al., "Measurement of Tacrolimus (FK506) and Its Metabolites: A Review of Assay Development and Application in Therapeutic Drug Monitoring and Pharmacokinetic Studies," Therapeutic Drug Monitoring, 1997, vol. 19, 338-351. Bose et al., "Characterization and Molecular Modeling of a Highly Stable Anti-Hepatitis B Surface Antigen scFv," Molecular Immunology, 2003, vol. 40, 617-631.
Hatfield R. M. et al., "Development of an Enzyme-Linked Immunosorbent Assay for the Detection of Humoral Antibody to *Pasteurella* Anatipestifer," Avian Pathology, 1987, vol. 16, 123-140.
Kricka et al., "Human Anti-Animal Antibody Interferences in Immunological Assays," Clinical Chemistry, 1999, vol. 45, 942-956.
Le Meur Y, et al., "CYP3A5*3 influences sirolimus oral clearance in de novo and stable renal transplant recipients," Clin Pharmacol Ther., 2006, 80(1), 51-60.
PCT International Search Report and Written Opinion for Application No. PCT/US07/88109, dated Sep. 24, 2008, 8 Pages.
PCT International Search Report for Application No. PCT/US07/88056, dated Aug. 25, 2008, 1 Page.
PCT International Search Report and Written Opinion for Application No. PCT/US07/88070, dated Oct. 8, 2008, 1 Page.
PCT International Search Report and Written Opinion for Application No. PCT/US07/88087, dated Sep. 24, 2008, 7 Pages.

(Continued)

*Primary Examiner* — Jacob Cheu
(74) *Attorney, Agent, or Firm* — Audrey L. Bartnicki; Jennifer Wahlsten, Weaver, Austin, Villeneuve & Sampson LLP

(57) ABSTRACT

The invention provides methods of preparing a test sample for use in an assay for detecting an analyte bound by an intracellular ligand. The methods typically involve contacting the test sample with an assay reagent comprising: a lysis reagent; and a protease that has proteolytic activity for said intracellular ligand; to form a mixture compatible for use in an immunoassay without subsequent extraction steps. Other aspects of the invention include related immunoassays and test kits.

44 Claims, 1 Drawing Sheet

FOREIGN PATENT DOCUMENTS

| | | |
|---|---|---|
| EP | 293892 A2 | 12/1988 |
| EP | 440044 A1 | 8/1991 |
| EP | 0471295 | 2/1992 |
| EP | 0471295 A1 | 2/1992 |
| EP | 693132 A1 | 1/1996 |
| EP | 753744 A2 | 1/1997 |
| EP | 693132 B1 | 12/1997 |
| EP | 973805 A1 | 1/2000 |
| EP | 1244800 A1 | 10/2002 |
| EP | 2118657 A2 | 11/2009 |
| WO | WO9005008 A1 | 5/1990 |
| WO | WO-9218527 A1 | 10/1992 |
| WO | WO-9219745 A1 | 11/1992 |
| WO | WO-9325533 A1 | 12/1993 |
| WO | WO-9424304 A1 | 10/1994 |
| WO | WO-9425022 A1 | 11/1994 |
| WO | WO-9425072 A1 | 11/1994 |
| WO | WO-9516691 A1 | 6/1995 |
| WO | WO-9525812 A2 | 9/1995 |
| WO | WO9525812 A3 | 10/1995 |
| WO | WO-9612018 A2 | 4/1996 |
| WO | WO-9613273 A1 | 5/1996 |
| WO | WO-9703654 A2 | 2/1997 |
| WO | WO9800696 A1 | 1/1998 |
| WO | WO-9845333 A1 | 10/1998 |
| WO | WO9853315 A1 | 11/1998 |
| WO | WO-0134816 A1 | 5/2001 |
| WO | WO-2008082974 A2 | 7/2008 |
| WO | WO-2008082979 A2 | 7/2008 |
| WO | WO-2008082982 A1 | 7/2008 |
| WO | WO-2008082984 A2 | 7/2008 |

OTHER PUBLICATIONS

PCT International Search Report for Application No. PCT/US07/88098, dated May 27, 2008, 1 page.

Sinha et al., "Electrostatics in Protein Binding and Function," Current Protein and Peptide Science, 2002, vol. 3, 601-614.

Sinha et al., "Understanding antibody-antigen associations by molecular dynamics simulations: Detection of important intra- and intermolecular salt bridges," Cell Biochem Biophys, 2007, vol. 47, 361-375.

Supplementary European Search Report of EP Patent Application No. EP07865858, dated Mar. 19, 2010, 10 pages total.

Tamura et al., "A Highly Sensitive Method to Assay FK-506 Levels in Plasma ,"A Transplantation Proceedings Reprint, 1987, vol. XIX (6), 23-29.

USPTO Office Action dated Aug. 21, 2009, cover sheet and pp. 1-10, Notice of references, Information Disclosure Statement by Applicant and considered by Examiner in U.S. Appl. No. 11/490,624.

Uwatoko et al., "Characterization of Clq-Binding IgG Complexes in Systemic Lupus Erythematosus," Clinical Immunology and Immunopathology, 1984, vol. 30, 104-116.

Watson J. D. et al., "The Introduction of Foreign Genes Into Mice", Recombinant DNA, 2nd Ed., W.H. Freeman & Co., New York, 1992, 225-272.

Supplementary European Search Report of EP Patent Application No. EP07869487, dated Mar. 19, 2010, 8 pages total.

Clarke W., et al., "Immunoassays for therapeutic drug monitoring and clinical toxicology," Drug monitoring and clinical chemistry, 2004, 5, 95-112.

Kronquist K. E., et al., "Mechanism of alteration of the functional fraction of lipoprotein lipase in rat heart," Life Sci., 1980, 27(13), 1153-1158.

Lee J. W., et al., "Tacrolimus (FK506): validation of a sensitive enzyme-linked immunosorbent assay kit for and application to a clinical pharmacokinetic study," Ther Drug Monit., 1997, 19(2), 201-207.

Simamora P, et al., "Solubilization of rapamycin," Int J Pharm., 2001, 213(1-2), 25-29.

Supplementary European Search Report of EP Patent Application No. EP07869508, dated Mar. 19, 2010, 12 pages total.

Wilson D., et al., "Multi-center evaluation of analytical performance of the microparticle enzyme immunoassay for sirolimus," Clin Biochem., 2006, 39(4), 378-386.

Supplementary European Search Report of EP Patent Application No. 07869499.9, dated Feb. 3, 2011, 6 pages total.

Melnikova, et al., "Antigen Binding Activity of Monoclonal Antibodies After Incubation with Organic Sovents," Biochemistry (Moscow), 2000, vol. 65, No. 11, pp. 1488-1499.

Murakami, et al., "On-chip micro-flow polystyrene bead-based immunoassay for quantitative detection of tacrolimus (FK506)," Analytical Biochemistry, 2004, vol. 334, pp. 111-116.

Supplementary European Search Report of EP Patent Application No. EP07869487, dated Mar. 19, 2010, issued Apr. 9, 2010, 9 pages total.

Supplementary European Search Report of EP Patent Application No. EP07865858, dated Mar. 19, 2010, issued Apr. 1, 2010, 9 pages total.

Supplementary European Search Report of EP Patent Application No. EP07869508, dated Mar. 19, 2010, issued Apr. 13, 2010, 11 pages total.

Supplementary European Search Report of EP Patent Application No. EP07861291, dated Jan. 11, 2010, issued Jan. 21, 2010, 11 pages total.

Supplementary European Search Report of EP Patent Application No. EP07869499 dated Jan. 21, 2011, Issued Feb. 3, 2011, 6 pages total.

PCT International Search Report and Written Opinion for Application No. PCT/US07/10076, mailed Jul. 11, 2008, 11 pages total.

PCT International Search Report and Written Opinion for Application No. PCT/US07/88056, mailed Aug. 25, 2008, 11 pages total.

PCT International Search Report and Written Opinion for Application No. PCT/US07/88070, mailed Oct. 8, 2008, 11 pages total.

PCT International Search Report and Written Opinion for Application No. PCT/US07/88087, mailed Sep. 24, 2008, 12 pages total.

PCT International Search Report and Written Opinion for Application No. PCT/US07/88098, mailed May 27, 2008, 7 pages total.

PCT International Search Report and Written Opinion for Application No. PCT/US07/88109, mailed Sep. 24, 2008, 15 pages total.

Murakami, et al., "On-chip micro-flow polystyrene bead-based immunoassay for quantitative detection of tacrolimus (FK506)", Analytical Biochemistry, vol. 334 (1) pp. 111-116 (2004).

Cogill J.L., et al., "Evaluation of the Tacrolimus, II Micro Particle Enzyme Immunossay (Meia II) in Liver and Renal Transplant Recipients," Clinical Chemistry, 1998, vol. 44 (9), pp. 1942-1946.

European Supplemental Search Report and Search Opinion dated Apr. 9, 2010 issued in EP07869487.4 (8 pages).

Melnikova Y. I., et al., "Antigen-binding activity of monoclonal antibodies after incubation with organic solvents.", Biochemistry. Biokhimii A, 2000, 65, 11, 1256-1265.

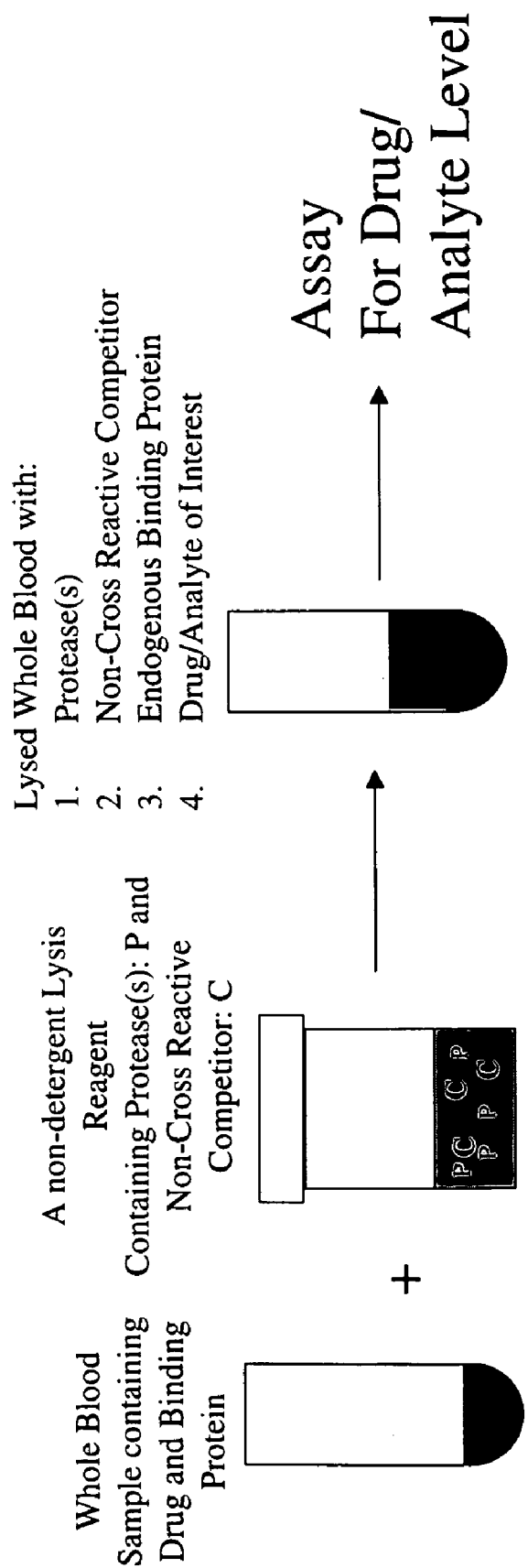

DIAGNOSTIC TEST FOR THE DETECTION OF A MOLECULE OR DRUG IN WHOLE BLOOD

CROSS REFERENCE TO RELATED APPLICATIONS

This application is a continuation application of PCT International Application PCT/US2007/088087 filed Dec. 19, 2007 (expired), and claims the priority of U.S. Provisional Application Ser. No. 60/882,732 filed Dec. 29, 2006 (expired), the disclosures of which are incorporated herein by reference in their entireties.

TECHNICAL FIELD

This invention relates to the use of one or more proteases in the preparation of samples for diagnostic assays to reduce or eliminate sample bias produced by freezing or storage of biological samples prior to assay.

BACKGROUND

Many analytes of clinical interest are taken up by cells or become complexed with one or more other components of the test sample. Accordingly, to obtain an accurate measurement of the amount of analyte present in the sample, it is necessary to treat the sample, and/or conduct the assay under conditions, such that the analyte is released from the cells or other component(s) for detection in the assay.

For example, immunosuppressant drugs such as tacrolimus, everolimus, temsorolimus and cyclosporine are effective for the treatment of organ or tissue rejection following transplant surgery, of graft versus host disease and of autoimmune diseases in humans. During immunosuppressant drug therapy, monitoring the blood concentration levels of the immunosuppressant is an important aspect of clinical care because insufficient drug levels lead to graft (organ or tissue) rejection and excessive levels lead to undesired side effects and toxicities. Blood levels of immunosuppressant are therefore measured so drug dosages can be adjusted to maintain the drug level at the appropriate concentration. Diagnostic assays for determination of immunosuppressant blood levels have thus found wide clinical use.

Initially, the immunosuppressant must be extracted and separated from the other components of the patient sample. The bulk of the immunosuppressant drug in the patient sample is present in a complex with various "carrier" molecules, such as binding proteins. Sirolimus, tacrolimus and cyclosporine are found predominately in the red blood cells of patient specimens and are associated with specific binding proteins, FKBP for sirolimus and tacrolimus, and cyclophilin for cyclosporine. To ensure an accurate measurement of the total drug concentration in the specimen, the drug bound to the binding proteins is preferably liberated prior to quantitation. This has been addressed by using detergents to lyse cells and/or organic solvents to denature the sample proteins.

Following its extraction from the binding proteins, the drug can be measured in a number of different ways, including by immunoassay or chromatography with absorbance or mass spectrophotometric detection. Immunoassays for immunosuppressant drugs are available in a variety of formats, but all use the binding of an antibody or binding protein (e.g., FKBP) to the immunosuppressant drug. A commonly used immunoassay is an assay which involves the binding of a first antibody to the immunosuppressant and the binding of labeled immunosuppressant (e.g., acridinium-sirolimus) to the remaining free antibody binding sites, followed by quantitation by detection of the label.

SUMMARY

This invention pertains to the discovery that one or more proteases can be incorporated into preparations (e.g., for immunoassays) to resolve an analyte (e.g., drug) concentration bias observed between using whole unlysed fresh samples (e.g., patient blood samples) and freeze-thawed lysed samples (e.g., calibrator diluent). It was also discovered that protease(s) are particularly useful in the preparation of samples for diagnostic assays in which a binding protein proteolyses over time, thus changing the affinity to its ligand (analyte), which, in turn, changes the concentration of the ligand detected in the diagnostic assay.

Thus, in certain embodiments, this invention provides methods of preparing a test sample for use in an assay for detecting an analyte bound by an intracellular ligand. The methods typically involve contacting said test sample (e.g., biological sample) with an assay reagent comprising a lysis reagent (or one or more components thereof); and a protease that has proteolytic activity for the intracellular ligand; to form a mixture compatible for use in an immunoassay without subsequent extraction steps. In various embodiments the test sample comprises whole blood or a blood fraction (e.g., serum). In various embodiments the test sample comprises human blood (e.g., blood from a human being treated with an immunosuppressant). In various embodiments the protease is selected from the group consisting of a serine protease, a metalloprotease, a thioprotease, an aspartic acid protease, and a glutamic acid protease. In certain embodiments the protease is selected from the group consisting of proteinase K, dispase, and trypsin. In various embodiments the lysis reagent comprises a glycol selected from the group consisting of ethylene glycol, propylene glycol, and an analog thereof; and at least one alcohol having five or fewer carbons (e.g., methanol, ethanol, propanol, and the like). In certain embodiments the ratio of glycol to alcohol is in the range of about 4:1 to about 1:4, more preferably about 4:1 to about 1:2. In certain embodiments the test sample is added to the lysis reagent (or to components of the lysis reagent) to form a mixture of sample:lysis reagent at a ratio in the range of about 2:1 to about 1:10, preferably about 2:1 to about 1:5, more preferably about 2:1 to about 1:2. In certain embodiments the method does not comprise centrifuging the sample. In certain embodiments, a detergent is not used to lyse or solubilize the test sample. In certain embodiments the method does not comprise contacting the test sample with a detergent. In certain embodiments the assay reagent further comprises a competitor that competes with the analyte for binding by the intracellular ligand, but is not substantially cross-reactive with the ligand (analyte) capture system (e.g., antibody or other capturing ligand) in the assay detection system. In certain embodiments the intracellular ligand is an immunophilin ligand. In certain embodiments the analyte comprises an immunosuppressant drug, and the competitor comprises a different, but structurally similar molecule (e.g., an analogue) that may or may not be an immunosuppressant drug). In certain embodiments the analyte comprises an immunosuppressant drug selected from the group consisting of tacrolimus, everolimus, zotarolimus, cyclosporine, and analogs of any of these compounds.

In certain embodiments this invention provides methods of preparing a test sample for use in an assay for detecting an analyte bound by an intracellular ligand. The methods typically involve contacting the test sample with a reagent comprising: a detergent-free lysing reagent; and a protease that has proteolytic activity for the intracellular ligand. In various embodiments the test sample comprises whole blood or a blood fraction (e.g., serum). In various embodiments the test sample comprises human blood (e.g., blood from a human being treated with an immunosuppressant). In various embodiments the protease is selected from the group consisting of a serine protease, a metalloprotease, a thioprotease, an aspartic acid protease, and a glutamic acid protease. In certain embodiments the protease is selected from the group consisting of proteinase K, dispase, and trypsin. In various embodiments the lysis reagent comprises a glycol selected from the group consisting of ethylene glycol, propylene glycol, and an analog thereof; and at least one alcohol having five or fewer carbons (e.g., methanol, ethanol, propanol, and the like). In certain embodiments the ratio of glycol to alcohol is in the range of about 4:1 to about 1:4, more preferably about 4:1 to about 1:2. In certain embodiments the test sample is added to the lysis reagent (or to components of the lysis reagent) to form a mixture of sample:lysis reagent at a ratio in the range of about 2:1 to about 1:10, preferably about 2:1 to about 1:5, more preferably about 2:1 to about 1:2. In certain embodiments the method does not comprise centrifuging the sample. In certain embodiments, a detergent is not used to lyse or solubilize the test sample. In certain embodiments the method does not comprise contacting the test sample with a detergent. In certain embodiments the assay reagent further comprises a competitor that competes with the analyte for binding by the intracellular ligand, but is not substantially cross-reactive with the ligand (analyte) capture system (e.g., antibody or other capturing ligand) in the assay detection system. In certain embodiments the intracellular ligand is an immunophilin ligand. In certain embodiments the analyte comprises an immunosuppressant drug, and the competitor comprises a different, but structurally similar molecule (e.g., an analogue) that may or may not be an immunosuppressant drug). In certain embodiments the analyte comprises an immunosuppressant drug selected from the group consisting of tacrolimus, everolimus, zotarolimus, cyclosporine, and analogs of any of these compounds.

Also provided is a method for assessing the concentration of an analyte (e.g., an immunosuppressant drug) in a test sample. The methods typically involve contacting a test sample with an assay reagent to produce an assay mixture compatible for use in an immunoassay without subsequent extraction steps, where the assay reagent comprises: a lysis reagent (or components thereof); and a protease that has proteolytic activity for an intracellular ligand that binds the analyte; and assaying the lysis mixture for the analyte (e.g., an immunosuppressant drug). In certain embodiments the assay mixture is a homogeneous mixture and/or the assay comprises an immunoassay. In certain embodiments the immunosuppressant drug is selected from the group consisting of sirolimus, tacrolimus, everolimus, zotarolimus, cyclosporine, and analogs of any of these compounds. In certain embodiments the test sample comprises a human blood sample (e.g., whole blood or a blood fraction (e.g., serum)).

In certain embodiments the method does not comprise centrifuging the sample. In certain embodiments, a detergent is not used to lyse or solubilize the test sample. In certain embodiments the method does not comprise contacting the test sample with a detergent. In certain embodiments the assay reagent further comprises a competitor that competes with the analyte for binding by the intracellular ligand, but is not substantially cross-reactive with the ligand (analyte) capture system (e.g., antibody or other capturing ligand) in the assay detection system. In certain embodiments the intracellular ligand is an immunophilin ligand. In certain embodiments the analyte comprises an immunosuppressant drug, and the competitor comprises a different, but structurally similar molecule (e.g., an analogue) that may or may not be an immunosuppressant drug). In certain embodiments the analyte comprises an immunosuppressant drug selected from the group consisting of tacrolimus, everolimus, zotarolimus, cyclosporine, and analogs of any of these compounds.

In certain embodiments this invention provides a test kit comprising at least one antibody or protein capable of binding specifically to at least one immunosuppressant drug (e.g., sirolimus, tacrolimus, everolimus, zotarolimus, cyclosporine, and an analog of any of these compounds); and an assay reagent comprising: a non-detergent lysing reagent (e.g., as described herein); and a protease that degrades an immunophilin ligand. In certain embodiments the non-detergent lysing reagent comprises: a glycol selected from the group consisting of ethylene glycol, propylene glycol, and an analog thereof; and at least one alcohol having five or fewer carbons. The kit can, optionally, additionally comprise a control composition comprising the at least one immunosuppressant drug. In certain embodiments the kit further comprises a competitor that competes with the analyte for binding by an intracellular ligand, but is not cross-reactive with the ligand (analyte) capture system (e.g., antibody or other capturing ligand) in the assay detection system. In certain embodiments the intracellular ligand is an immunophilin ligand. In certain embodiments the analyte comprises an immunosuppressant drug, and the competitor comprises a different, but structurally similar molecule (e.g., an analogue) that may or may not be an immunosuppressant drug). In certain embodiments the analyte comprises an immunosuppressant drug selected from the group consisting of tacrolimus, everolimus, zotarolimus, cyclosporine, and analogs of any of these compounds. In certain embodiments the competitor is provided in the assay reagent. In certain embodiments the intracellular ligand is an immunophilin ligand. In various embodiments the competitor comprises an immunosuppressant drug that is different from, but structurally similar to, the immunosuppressant drug being assayed.

BRIEF DESCRIPTION OF THE DRAWINGS

FIG. 1 schematically illustrates one embodiment of the sample preparation methods described herein.

DETAILED DESCRIPTION

This invention relates generally to the use of one or more proteases in the preparation of samples for diagnostic assays to reduce or eliminate sample bias produced by freezing or storage of biological samples prior to assay.

DEFINITIONS

Terms used in the claims and specification are defined as set forth below unless otherwise specified.

An "immunosuppressant drug" or "immunosuppressant", as used herein, refers to a therapeutic compound, either small molecule or antibody based, that has the same or similar chemical structure to either rapamycin (sirolimus) or cyclosporine, also known as cyclosporin A. Any known or hereafter developed analog of either rapamycin or cyclosporine is considered an immunosuppressant herein. Preferred immunosuppressants include sirolimus, tacrolimus, everolimus, temsorolimus, zotarolimus and cyclosporine. Tacrolimus and cyclosporine are calcineurin inhibitors that suppress early activation of the immune system's T lymphocytes through inhibition of cytokines such as interleukin 2. In contrast, the primary target of sirolimus, everolimus and zotarolimus is mammalian target of rapamycin (mTOR), a specific cell-cycle regulatory protein. The inhibition of mTOR leads to suppression of cytokine-driven T-lymphocyte proliferation.

The chemical formula of cyclosporine is in Formula A. The chemical formula of sirolimus (rapamycin) is in Formula B. The chemical formula of the structural difference of everolimus (RAD) from sirolimus is in Formula C.

meric form (K. C. Nicolaou et al., *J. Am. Chem. Soc.*, 1993, 115, 4419-4420; S. L. Schreiber, *J. Am. Chem. Soc.*, 1993, 115, 7906-7907; S. J. Danishefsky, *J. Am. Chem. Soc.*, 1993, 115, 9345-9346. The invention comprises lysis reagents, lysis methods, assays and assay kits for rapamycin or any of its analogs.

Another immunosuppressant analog of rapamycin is FK-506, also known as tacrolimus, which was isolated from a strain of *S. tsukubaensis*. FK-506's chemical formula is published in European Patent EP 0 293 892 B1. Analogs of FK-506 include, but are not limited to, the related natural

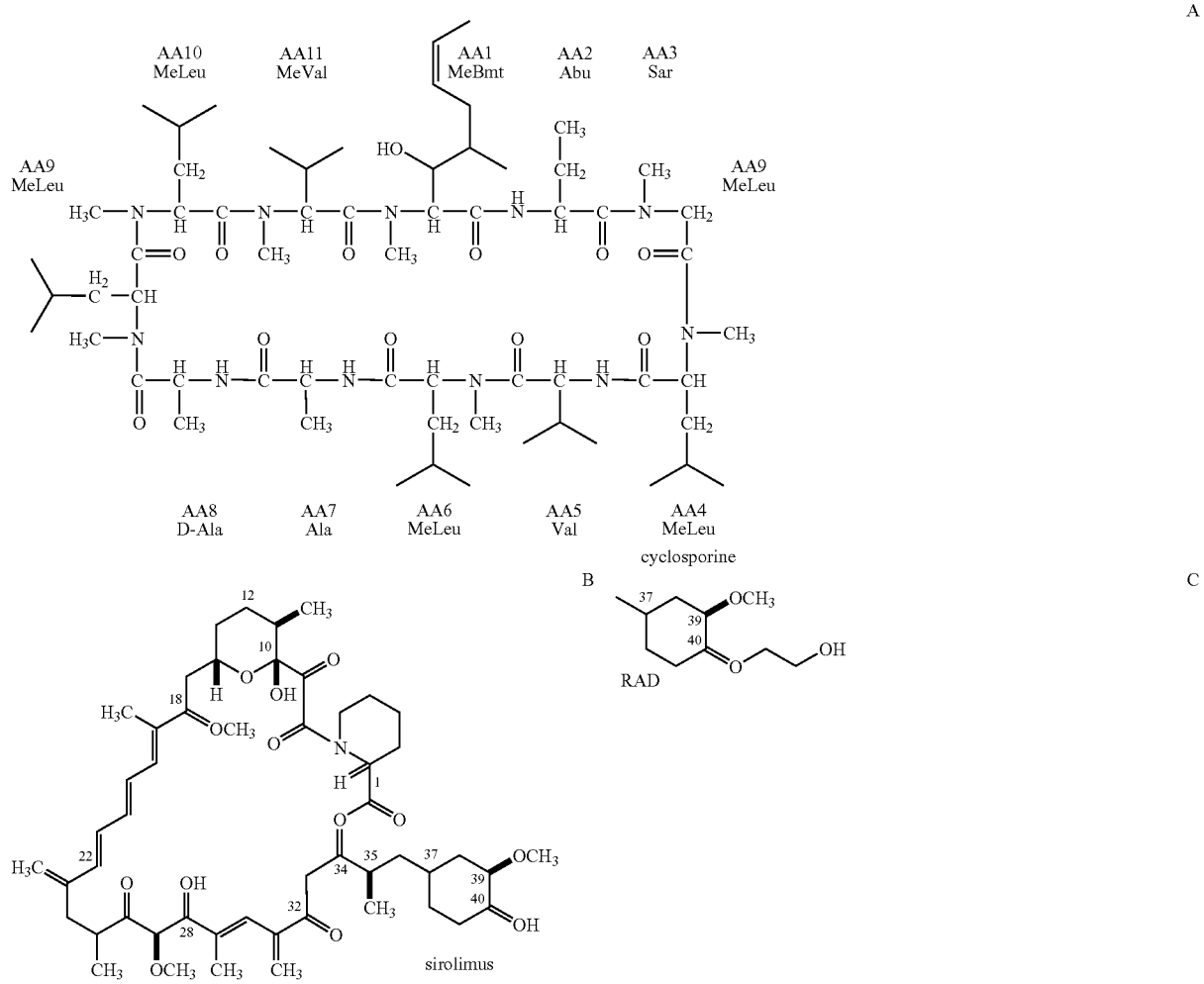

Numerous derivatives or analogs of cyclosporine have been prepared. The invention comprises lysis reagents, lysis methods, assays and assay kits for cyclosporine or any of its analogs.

Numerous derivatives or analogs of rapamycin have been prepared. For example, these include the preparation of ester mono- and di-ester derivatives of rapamycin (PCT International Application WO 92/05179), 27-oximes of rapamycin (EP Patent 0 467606); 42-oxo analog of rapamycin (U.S. Pat. No. 5,023,262); bicyclic rapamycins (U.S. Pat. No. 5,120, 725); rapamycin dimers (U.S. Pat. No. 5,120,727); silyl ethers of rapamycin (U.S. Pat. No. 5,120,842); and arylsulfonates and sulfamates (U.S. Pat. No. 5,177,203). Rapamycin was recently synthesized in its naturally occurring enantioproducts FR-900520 and FR-900523, which differ from FK-506 in their alkyl substituent at C-21, and were isolated from *S. hygroscopicus yakushimnaensis*. Another analog, FR-900525, produced by *S. tsukubaensis*, differs from FK-506 in the replacement of a pipecolic acid moiety with a proline group. A large number of compounds that retain the basic structure and immunological properties of FK 506 are described in a number of publications, for example: European Patents EP Patent 184162, EP Patent 315973, EP Patent 323042, EP Patent 423714, EP Patent 427680, EP Patent 465426, EP Patent 484936, EP Patent 532088, and EP Patent 474126; PCT International Applications WO 91/13889, WO 91/19495, and WO 93/5059; and the like. The invention comprises lysis reagents, lysis methods, assays and assay kits for FK-506 or any of its analogs. Temsorolimus is another ester derivative of sirolimus which can be monitored with the invention.

ABT-578[40-epi-(1-tetrazolyl)-rapamycin], known better today as zotarolimus, is a semi-synthetic macrolide triene antibiotic derived from rapamycin. Zotarolimus' structure is shown in Formula D.

one "light" (about 25 kD) and one "heavy" chain (about 50-70 kD). The N-terminus of each chain defines a variable region of about 100 to 110 or more amino acids primarily responsible for antigen recognition. The terms "variable light chain (VL)" and "variable heavy chain (VH)" refer to these light and heavy chains respectively.

The isomers of zotarolimus

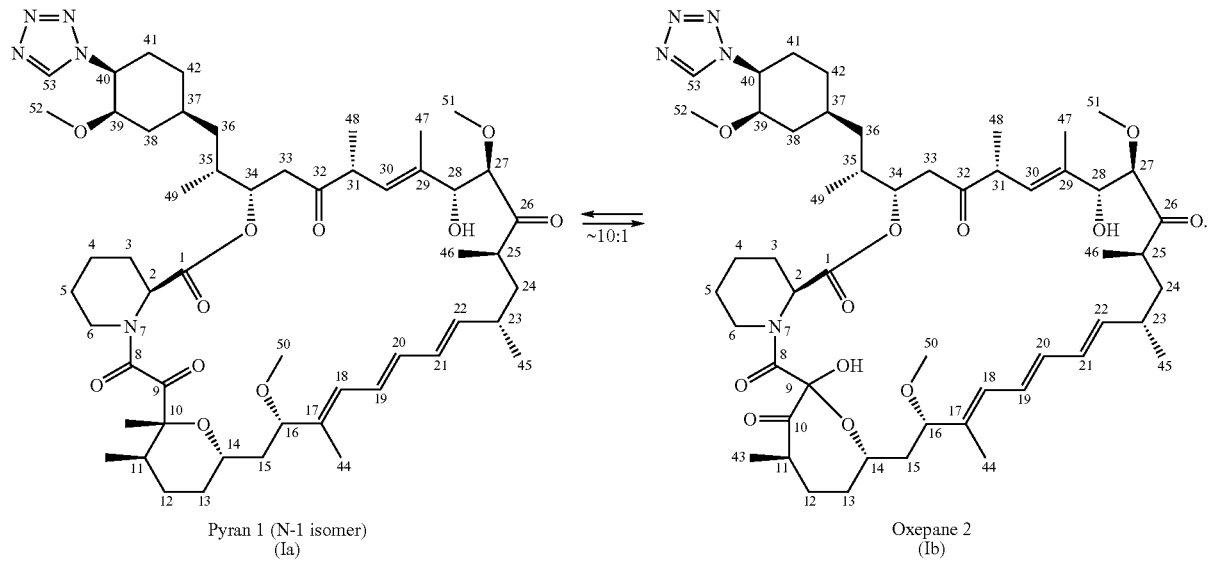

Pyran 1 (N-1 isomer)
(Ia)

Oxepane 2
(Ib)

Formula D

As used herein with reference to an immunosuppressant drugs, the term "structurally similar" indicates that the drugs have sufficiently similar structures that the drugs bind competitively to at least one common binding partner (e.g., a binding protein).

The term "test sample" refers to a component, tissue or fluid of an animal's body that is the source of the immunosuppressant drug analyte. These components, tissues and fluids include human and animal body fluids such as whole blood, serum, plasma, synovial fluid, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens; and fixed cell specimens. Preferably, the test sample is a human peripheral blood sample.

As used herein, an "antibody" refers to a protein consisting of one or more polypeptides substantially encoded by immunoglobulin genes or fragments of immunoglobulin genes. This term encompasses polyclonal antibodies, monoclonal antibodies, and fragments thereof, as well as molecules engineered from immunoglobulin gene sequences. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having Antibodies exist as intact immunoglobulins or as a number of well-characterized fragments produced by digestion with various peptidases. Thus, for example, pepsin digests an antibody below the disulfide linkages in the hinge region to produce F(ab')2, a dimer of Fab which itself is a light chain joined to VH-CH1 by a disulfide bond. The F(ab')2 may be reduced under mild conditions to break the disulfide linkage in the hinge region thereby converting the (Fab')2 dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology.

Thus, the term "antibody," as used herein, also includes antibody fragments either produced by the modification of whole antibodies or synthesized de novo using recombinant DNA methodologies. The term "antibody" also encompasses single chain antibodies (antibodies that exist as a single polypeptide chain), more preferably single chain Fv antibodies (sFv or scFv), in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker (Huston, et al. (1988) Proc. Nat. Acad. Sci. USA, 85: 5879-5883). While the VH and VL are connected to each as a single polypeptide chain, the VH and VL domains associate non-covalently. The scFv antibodies and a number of other structures convert the naturally aggregated, but chemically separated, light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778).

"Analyte," as used herein, refers to the substance to be detected, which may be suspected of being present in the test sample. The analyte can be any substance for which there exists a naturally occurring specific binding partner or for which a specific binding partner can be prepared. Thus, an analyte is a substance that can bind to one or more specific binding partners in an assay.

A "binding partner," as used herein, is a member of a binding pair, i.e., a pair of molecules wherein one of the molecules binds to the second molecule. Binding partners that bind specifically are termed "specific binding partners." In addition to the antigen and antibody binding partners commonly used in immunoassays, other specific binding partners can include biotin and avidin, carbohydrates and lectins, complementary nucleotide sequences, effector and receptor molecules, cofactors and enzymes, enzyme inhibitors and enzymes, and the like. Immunoreactive specific binding partners include antigens, antigen fragments, antibodies and antibody fragments, both monoclonal and polyclonal, and complexes thereof, including those formed by recombinant DNA methods.

The term "specific binding" is defined herein as the preferential binding of binding partners to another (e.g., a polypeptide and a ligand (analyte), two polypeptides, a polypeptide and nucleic acid molecule, or two nucleic acid molecules) at specific sites. The term "specifically binds" indicates that the binding preference (e.g., affinity) for the target molecule/sequence is at least 2-fold, more preferably at least 5-fold, and most preferably at least 10- or 20-fold over a non-specific target molecule (e.g. a randomly generated molecule lacking the specifically recognized site(s)).

An antibody that specifically binds an immunosuppressant drug is said to be "specific for" that immunosuppressant drug.

The terms "capture reagent" or "capture agent" refer to a binding partner that binds to analyte, more preferably that specifically binds to an analyte. In various embodiments capture agents can be attached to a solid phase. As used herein, the binding of a solid phase-affixed capture agent to analyte forms a "solid phase-affixed complex."

The term "labeled detection agent" is used herein to refer to a binding partner that binds to analyte, preferably specifically, and is labeled with a detectable label or becomes labeled with a detectable label during use in an assay.

A "detectable label" includes a moiety that is detectable or that can be rendered detectable.

As used with reference to a labeled detection agent, a "direct label" is a detectable label that is attached, by any means, to the detection agent.

As used with reference to a labeled detection agent, an "indirect label" is a detectable label that specifically binds the detection agent. Thus, an indirect label includes a moiety that is the specific binding partner of a moiety of the detection agent. Biotin and avidin are examples of such moieties that are employed, for example, by contacting a biotinylated antibody with labeled avidin to produce an indirectly labeled antibody.

As used herein, the term "indicator reagent" refers to any agent that is contacted with a label to produce a detectable signal. Thus, for example, in conventional enzyme labeling, an antibody labeled with an enzyme can be contacted with a substrate (the indicator reagent) to produce a detectable signal, such as a colored reaction product.

As used herein, a "glycol analog" is any glycol having from two to six carbon atoms.

A lysis mixture is said to be "homogeneous" when it is sufficiently free of large particulates to allow accurate and reliable pipetting (either manually or using an automated system).

The phrase "without subsequent extraction steps" when used with respect to an assay mixture indicates that the assay mixture is ready "as is" for immunoassay (as described herein). Thus, no further centrifugation is required prior to analysis. The mixture can be ready for application to an analyzer.

I. The Use of Proteases to Reduce or Eliminate Assay Bias.

The invention pertains to the use of a protease or proteases in sample preparations (e.g., for immunoassays) to resolve an analyte (e.g., drug) concentration bias observed between using whole unlysed fresh blood (e.g., patient specimens) and freeze-thawed lysed blood (e.g., calibrator diluent). The protease(s) are particularly useful in the preparation of samples for diagnostic assays in which a binding protein proteolyses over time, thus changing the affinity to its ligand (analyte), which, in turn, changes the concentration of the ligand detected in the diagnostic assay.

Intracellular binding proteins, such as hormone receptors, G-proteins, protein kinases, protein phosphatases, isomerases, and the like, often bind a target analyte that is to be assayed, for example, in a diagnostic assay. Thus, for example, immunophilins often bind immunosuppressant drugs such as rapamycin (sirolimus), tacrolimus, everolimus, temsorolimus, zotarolimus, cyclosporine, and the like. The intracellular binding proteins are typically protected from the external environment (e.g. extracellular matrix) by the cell membrane. When this membrane is lysed, proteases gain access to these intracellular binding proteins and can alter their binding affinities to the associated target analyte (e.g., drug, small molecule, etc.).

These lysis events present a significant diagnostic problem, since samples are often stored frozen or for prolonged periods of time, both of which lead to cell lysis and proteolysis of intracellular proteins. Thus, a testing bias is introduced into assays for analytes bound by such proteins since in fresh samples the intracellular binding proteins may be relatively intact and have greater affinity for the analyte(s) than the intracellular binding proteins in stored samples.

In certain embodiments this invention pertains to the discovery that, especially where the analyte is a non-protein molecule, one or more proteases can be used in sample preparations to facilitate the release of the analyte from its binding protein and thereby reduce or eliminate this bias. This permits more consistent measurements of the analyte.

It was also a surprising discovery that proteases were effective to reduce or eliminate assay bias (e.g., due to analyte binding by intracellular ligand(s)) in sample preparations without the use of detergents (e.g., lysis detergents) and/or without the use of other denaturant compositions or methods (e.g., organic solvents, low pH, high pH, chaotrops, and the like). Elimination of the use of such agents facilitates the use of homogeneous detection methods that also reduce variance in analyte measurement.

The proteases are particularly useful in the preparation of samples for diagnostic assays in which a binding protein proteolyses over time, thus changing the affinity to its ligand (analyte), which, in turn, changes the concentration of the ligand detected in the diagnostic assay. The use of a protease in sample preparation and/or, in certain embodiments, the assay itself, hastens this process so the ligand always or primarily interacts with a proteolyzed form of the binding protein. Thus, the ligand (analyte) concentrations remain substantially constant thereby reducing variance in the assay and/or reducing or eliminating bias produced by storage of a sample prior to assay.

In certain embodiments the proteases are used in conjunction with a non-cross reactive competitor to aid in the release of the ligand (analyte) form its binding protein, thus requiring a smaller change in the binding protein than would otherwise be necessary if no competitor were employed.

It is noted that while the discussion provided herein focuses on immunosuppressant drugs as target analytes, the methods are equally applicable to other analytes that are bound by intracellular binding proteins, preferably non-protein analytes.

Suitable proteases include, but are not limited to serine proteases (e.g., trypsin, chymotrypsin, elastase, etc.), metalloproteases (e.g., dispase, thermolysin, etc.), thioproteases (e.g., papain, cathepsins, etc.), aspartic acid proteases (e.g., plasmepsins), glutamic acid proteases, and the like, and combinations thereof. The protease(s) selected for use in a particular assay preparation are typically ones that can degrade the binding protein, thereby releasing the analyte (e.g., immunosuppressant drug) for assay. In certain embodiments proteases are selected that can be inactivated without adversely affecting the sensitivity and the precision of the assay to be carried out. The proteases are preferably provided in forms that are free from other contaminating enzymes that might not be inactivated by the method of inactivation used. Otherwise, any residual proteolytic activity could degrade an antibody used in a subsequent immunoassay.

Proteases are available from a number of commercial suppliers including, but not limited to Sigma, Aldrich, Boehringer Mannheim, Calbiochem, and the like. In certain embodiments exemplary proteases include, but are not limited to, proteinase K, subtilisin, pepsin, dispase, thermolysin, chymotrypsin (including $\alpha$-, $\beta$-, $\gamma$-, $\delta$-, or $\pi$-chymotrypsin), trypsin, ficin, bromelain, and the like, and combinations thereof.

Proteinase K (Sigma Chemical Co., St. Louis, Mo.) is a nonspecific, Ca-dependent protease that can be inactivated by heat (65° C. or higher) and by specific protease inhibitors, including, but not limited to phenyl methyl sulfonyl fluoride (PMSF, Boehringer Mannheim, Indianapolis, Ind.), or diisopropylfluorophosphate (DFP, Calbiochem, La Jolla, Calif.). Subtilisin (Sigma) is also a nonspecific, Ca-dependent protease that can be inactivated by heat (55° C. or higher), although it can be inhibited by acidic pH or a specific protease inhibitor, such as PMSF, DFP or aprotinin.

Dispase (Boehringer Mannheim or Sigma or Calbiochem) and thermolysin (Sigma or Boehringer Mannheim) are Ca-dependent metalloproteases that can be inactivated by EDTA, at a concentration of about 5 mM, for example. In certain embodiments, when dispase and thermolysin combined are used as the protease, proteolysis can be inactivated by addition of a divalent cation chelator, such as EDTA, at a concentration of about 5 mM, for example, in the presence of a zinc salt, e.g., $ZnSO_4$, at a concentration of about 40 mM, for example.

Trypsin (Worthington Biochemical Corp., Freehold, N.J.) cleaves proteins specifically at the carboxyl side of lysine or arginine residues and can be inhibited by heat (90° C. or higher) or specifically inhibited by many agents, including, but not limited to aprotinin (Aprotinin injection formerly marketed as Trasylol®, by Bayer, West Haven, Conn.; inhibitor still available from Calbiochem, La Jolla, Calif., and other vendors), leupeptin (Sigma-Aldrich, St. Louis, Mo. or Boehringer Mannheim), PMSF, or specific trypsin inhibitors derived from soybean, lima bean or egg white (Worthington Biochemical Corp., Freehold, N.J. or Sigma-Aldrich, St. Louis, Mo.). Ficin is a thiol protease that can be inactivated by $HgCl_2$, at a concentration of about 2 mM, for example. Bromelain is also a thiol protease (thioprotease) and can be inactivated by bromelain inhibitor (Sigma-Aldrich, St. Louis, Mo.).

In particular embodiments, the concentration of protease(s) is high enough to degrade to the binding proteins within about 2-4 hours, preferably within about 1 hour, more preferably within about 30 minutes, and still more preferably within about 20 minutes or 10 minutes, yet low enough to allow efficient inactivation of the enzyme. Accordingly, the concentration of protease preferably ranges from about 0.1 to 5.0 units/mL, more preferably from about 0.3 to about 3 units/mL, still more preferably from about 0.5 to 2.0 units/mL, and most preferably about 1 units/mL.

As indicated above, the use of one or more proteases, as described herein can obviate the need to use denaturants. This is advantageous as the use of denaturants typically requires subsequent centrifugation steps to remove precipitated blood constituents, which reduces the efficiency of this approach. Additionally, the use of organic solvents at the concentration(s) required can lead to sample evaporation that is significant enough to affect analyte concentration.

In certain embodiments, where the analyte (e.g., immunosuppressant drug) binds to one or more binding proteins in the test sample (e.g., immunophilins), the methods described herein can, optionally, additionally entail contacting the sample with one or more agent(s) (in addition to the protease(s)) that release the analyte from the binding protein(s). For example, the agent(s) can include agents that compete (competitors) with the analyte for binding to the binding protein(s). The agent is generally selected so that it will not affect the results of the assay to be carried out. Thus, an agent is preferably selected that is not reactive (e.g., is not bound by) the analyte detection system (e.g., capture agent), or is substantially less reactive (e.g., at least 10-fold less reactive, preferably at least 100-fold less reactive, more preferably at least 1000-fold, or 10,000-fold less reactive) with the analyte detection system (capture agent).

Thus, for instance, if the assay is an immunoassay, the agent (competitors) is typically one that the relevant antibody does not substantially cross-react with. In certain embodiments, where the analyte is an immunosuppressant drug, the agent can be a different, but structurally similar analogue that may, or may not, be an immunosuppressant drug. For example, sirolimus and tacrolimus both bind FKBP, and, for this reason, sirolimus can be used to release tacrolimus from FKBP and vice versa. Typically, in such instances, subsequent immunoassays will generally employ an antibody that distinguishes between sirolimus and tacrolimus. U.S. Pat. No. 6,187,547 (issued Feb. 13, 2001 to Legay and Wenger; incorporated herein by reference in its entirety for its teachings regarding immunosuppressant drug competition) describes "binding competitors" useful for releasing immunosuppressant drugs from binding proteins. Examples include: [$Thr^2$, $Leu^5$, $D-Hiv^8$, $Leu^{10}$]-Ciclosporin, which can release cyclosporin. In addition, U.S. Patent application 2005/112778 A1, published May 26, 2005, which is incorporated herein by reference, discloses derivatives of FK 506 that can act as a binding competitor to displace FK 506 or rapamycin from their immunophilin complexes.

In certain embodiments the methods described herein involve the use of detergent-free lysis reagents. The use of detergents can be problematic, in particular formats because the quantity of detergent needed to quickly lyse and fragment cells can cause foaming, which is unacceptable for samples that must be pipetted by most automated pipetting systems, and can interfere with immunochemistry in samples to be analyzed by immunoassays. The use of a detergent-free lysis reagent produces a sample that is not susceptible to foaming and eliminates the need for detergents, thus avoiding detergent driven interferences in assay immunochemistry.

The use of one or more proteases, as described herein, particularly in combination with a detergent-free lysis reagent produces a homogeneous mixture that is suitable for use in automated pipetting systems without the need for a centrifugation step and eliminates the use of substantial concentrations of volatile organic solvents.

II. Sample Collection and Processing

The methods of the invention are generally carried out on test samples derived from an animal, preferably a mammal, and more preferably a human. In certain instances (where the analyte comprises one or more immunosuppressants), the test sample is a test sample from a human (or veterinary animal) under treatment with an immunosuppressant (e.g., to prevent or inhibit transplant organ rejection, graft rejection, or for treatment of autoimmune disease).

The methods of the invention can be carried out using any sample that may contain the target analyte (e.g., immunosuppressant drug), such as a blood sample. In certain embodiments the test sample can comprise whole blood, or a blood fraction (e.g., serum).

The sample is collected by any standard technique. The sample can be immediately processed or stored (e.g., dried, frozen, stored under inert gas, and the like) for later processing. As desired, sample can be contacted directly with one or more proteases, as described herein, and a lysis reagent (or components thereof). In various embodiments the sample may, alternatively, be processed (e.g., reconstituted, diluted, buffered, fractionated, and the like) prior to treatment with the protease(s) and lysis reagent(s) or components thereof. In various embodiments the protease(s) are contacted with the sample, prior to, at the same time as, or after the sample is contacted with the lysis reagent(s) or components thereof.

One simple method is illustrated in FIG. 1, where the sample (in this case whole blood) is contacted with a non-detergent lysing reagent containing one or more protease(s) (P) and one or more non-cross reactive competitor(s) (C). This produces a homogeneous mixture comprising lysed whole blood, one or more protease(s), the non-cross-reactive competitor(s), the endogenous binding protein(s), and the analyte of interest (e.g., an immunosuppressant drug). The mixture is ready for assay.

In certain embodiments a detergent-free lysis reagent is utilized. Certain suitable lysis reagents include at least one glycol having from two to six carbon atoms and at least one alcohol having ten or fewer, preferably eight or fewer, more preferably five or fewer carbons. Glycols suitable for use in the lysis reagent include, for example, ethylene glycol, propylene glycol, and analogs thereof, as well as mixtures of such glycols. Alcohols suitable for use in the lysis reagent primarily include alcohols having a single hydroxyl group. Such alcohols include, but are not limited to primary alcohols (e.g., methanol, ethanol, isobutyl alcohol, etc.), secondary alcohols (e.g. isopropanol, cyclohexanol, etc.), and tertiary alcohols (e.g., tert-butanol, tert-amyl alcohol, etc.). In certain embodiments the alcohols include, but are not limited to, methanol, ethanol, and $C_3$-$C_{10}$ alcohols (e.g., propanol, pentanol, hexanol, septanol octanol, and the like), and mixtures thereof. In particular embodiments, the ratio of glycol to alcohol is in the range of about 4:1 to about 1:4 (volume: volume). In more particular embodiments, the ratio of glycol to alcohol is in the range of about 4:1 to about 1:2, preferably about 2:1 to about 1:2.

The lysis mixture can formed by any mixing technique at any desirable temperature to contact any chosen amount of the sample with the lysis reagent. The sample is contacted with a sufficient volume of lysis reagent to lyse the cells in the sample and produce a homogeneous mixture. For a lysis reagent wherein the ratio of glycol to alcohol is in the range of about 4:1 to about 1:4, as described above, sample can be added to the lysis reagent at a ratio in the range of about 2:1 to about 1:2, e.g., about 1:1 (volume:volume), depending on the lysis reagent composition. For example, about 100 μL to about 600 μL of blood sample can be mixed with about 50 μL to about 1200 μL of the lysis reagent for up to about five minutes. In certain embodiments, the lysis mixture is formed by mixing 150 μL of blood sample with 300 μL of lysis reagent and vortexing vigorously for 5-10 seconds. In preferred embodiments, lysis is complete in less than a minute at room temperature. The lysis mixture is then assayed for the analyte using a suitable assay. In preferred embodiments, the lysis mixture is produced, ready for analysis, without the need to centrifuge the sample.

In various embodiments the sample need not be contacted with the "mixed" lysis reagent, but can be mixed with one component of the lysis reagent (e.g., alcohol or glycol) and then the other component added to produce a complete lysis reagent as described above.

The lysis reagent of the invention can be employed without any added detergent. However, in certain embodiments, one or more detergents can be added, if desired. Detergents typically do not foam in the presence of the lysis reagent described above, and thus lysis mixtures prepared according to the invention can be amenable to automated pipetting, regardless of whether a detergent is included. If included in a lysis mixture intended for immunoassay, the detergent is preferably present at a concentration that does not interfere with the immunochemistry. Preferably, the detergent is a non-ionic detergent, such as saponin, and is employed at a concentration in the range of about 0.01% to 0.1%, more preferably about 0.1%. U.S. Pat. No. 5,650,288 (issued Jul. 22, 1997 to MacFarlane and Jensen; hereby incorporated by reference in its entirety for its teachings regarding detergent use) describes the use of detergents in immunoassays.

After lysis and release from binding proteins, if applicable, the analyte can be measured using any standard technique for detecting that analyte, e.g., immunoassay or chromatography with absorbance or mass spectrophotometric detection. For detection of immunosuppressant drugs, immunoassays are conveniently employed.

III. Immunoassays

A. In General

Immunoassays according to the invention can be used for the qualitative identification and/or the quantification of analyte in a test sample. These methods are applicable, for example, to immunoassays of immunosuppressant drugs, such as rapamycin (sirolimus), tacrolimus, everolimus, temsorolimus, zotarolimus, cyclosporine, and analogs of any of these compounds.

Such immunoassays can be carried out by combining one or more proteases, as described herein, and, optionally, a lysis reagent, or one or more components thereof, with the test sample to form a lysis mixture, as described above. The lysis mixture can be contacted with at least one antibody specific for the analyte under conditions suitable for binding of the antibody to the analyte, if present, to form an assay mixture, and binding of the antibody to the analyte is then detected.

In certain embodiments, enhanced assay sensitivity can be achieved by contacting the lysis mixture with the antibody in the presence of a salt concentration of greater than about 0.4 M (e.g., from about 0.5 M to about 5.0 M). In particular embodiments, the salt concentration is less than or equal to about 4.0 M (e.g., from about 0.5 M to about 4.0 M). In exemplary embodiments, the salt concentration is about 2.0 M (e.g., from about 1.5 M to about 2.5 M, particularly about 1.8 M, about 1.9 M, about 2.0 M, about 2.1 M, or about 2.2 M). Suitable salts can include, for example, any of the following anions: fluoride, chloride, bromide, iodide, thiocyanate, acetate, citrate, and bisulfate. In particular embodiments, the salt includes a monovalent anion, such as, for example: fluoride, chloride, bromide, iodide, thiocyanate, and acetate. In preferred embodiments, the salt includes chloride, e.g., a chloride salt of an alkali metal (e.g., lithium, sodium, potassium, rubidium, cesium). Generally, the salt employed is soluble under the assay conditions. Sodium chloride is highly soluble under most conditions, and can thus be conveniently used to enhance assay sensitivity in a wide variety of immunoassays according to the invention.

The salt can be provided to the assay mixture in any convenient manner and can be present before, or added after, contact between the lysis mixture and the antibody. In particular embodiments, the salt is provided in an assay diluent, which can also optionally include one or more other components, in addition to water (such as, for example, a buffer). The salt concentration in the assay diluent will vary, depending on the desired final salt concentration and on the amount of diluent added to the assay mixture. For example, an assay diluent having a salt concentration of about 4.0 M could be added to an equal volume of assay mixture to provide a final salt concentration of about 2.0 M.

B. Antibodies

In immunoassays for the qualitative or quantitative detection of an analyte in a test sample, at least one antibody that binds to the analyte is contacted with a lysis mixture suspected of containing the analyte to form an antibody-analyte immune complex. To detect immunosuppressant drugs, any suitable antibodies that bind to the particular drug can be used in an immunoassay according to the invention. Antibodies to each of rapamycin (sirolimus), tacrolimus, zotarolimus, cyclosporine and everolimus are known in the art and/or are commercially available, and any of these can be used. In certain embodiments, it is preferred to use the monoclonal antibody that is a component of Abbott Laboratories' commercially available IMx® Sirolimus assay (Abbott Laboratories, Abbott Park, Ill.) for measuring sirolimus, or any other Sirolimus assay kit marketed by Abbott Laboratories (e.g., for use on a different commercial automated platform).

An illustrative protocol for producing an antibody specific for an immunosuppressant drug is as follows. Female RBf/Dnj mice are administered 3 monthly boosts of a drug-27-CMO-tetanus toxoid immunogen followed by an immunization with drug-42-HS-tetanus toxoid preparation on the 4th month. Seven months later, an intrasplenic pre-fusion boost is administered to the animal using the drug-27-CMO-tetanus toxoid immunogen 3 days prior to the fusion. Splenic B-cells are then isolated and used in a standard polyethylene (PEG) fusion with the SP2/0 myeloma. Confluent cultures are screened for anti-drug activity 10-14 days later in a microtiter EIA and positive cultures are then cloned using limiting dilution cloning technique. The resulting clones are isolated and scaled up in IMDM w/FBS (Invitrogen Corp., Carlsbad, Calif.) tissue culture medium and the secreted antibody is affinity purified using Protein A. An illustrative, preferred antibody generated using sirolimus as the drug can be used in immunoassays for sirolimus, everolimus and zotarolimus.

An illustrative, preferred antibody for use in immunoassays for tacrolimus is described in M. Kobayashi et al., "A Highly Sensitive Method to Assay FK-506 Levels in Plasma", at pp 23-29 of "FK-506 A Potential Breakthrough in Immunosuppression", *A Transplantation Proceedings Reprint*, Supplement 6, Vol. XIX, October, 1987, Editors T. Starzl, L. Makowka and S. Todo, published by Grune & Stratton, Inc., Philadelphia, Pa.

An illustrative, preferred antibody for use in immunoassays for cyclosporin is the monoclonal antibody that is a component of Abbott Laboratories' commercially available AxSYM cyclosporine assay for measuring cyclosporine.

C. Detection

The antibody-analyte immune complexes can then detected using any suitable technique. For example, the antibody can be labeled with a detectable label to detect and/or quantify the presence of the antibody-analyte complex. The selection of a particular label is not critical, but the chosen label must be capable of producing a detectable signal either by itself or in conjunction with one or more additional substances.

Useful detectable labels, their attachment to antibodies and detection techniques therefore are known in the art. Any detectable label known in the art can be used. For example, the detectable label can be a radioactive label, such as, $^3$H, $^{125}$I, $^{35}$S, $^{14}$C, $^{32}$P, $^{33}$P; an enzymatic label, such as horseradish peroxidase, alkaline peroxidase, glucose 6-phosphate dehydrogenase, etc.; a chemiluminescent label, such as, acridinium derivatives, luminol, isoluminol, thioesters, sulfonamides, phenanthridinium esters, etc.; a fluorescent label, such as, fluorescein (5-fluorescein, 6-carboxyfluorescein, 3'6-carboxyfluorescein, 5(6)-carboxyfluorescein, 6-hexachlorofluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, *Introduction to Immunocytochemistry*, 2$^{nd}$ ed., Springer Verlag, N.Y. (1997) and in Haugland, *Handbook of Fluorescent Probes and Research Chemi* (1996), which is a combined handbook and catalogue published by Molecular Probes, Inc., Eugene, Oreg., each of which is incorporated herein by reference. Preferred labels for use with the invention include chemiluminescent labels such as acridinium-9-carboxamide. Additional detail can be found in Mattingly, P. G., and Adamczyk, M. (2002) Chemiluminescent N-sulfonylacridinium-9-carboxamides and their application in clinical assays, in *Luminescence Biotechnology: Instruments and Applications* (Dyke, K. V., Ed.) pp 77-105, CRC Press, Boca Raton.

The detectable label can be bound to the analyte or antibody either directly or through a coupling agent. An example of a coupling agent that can be used is EDAC (1-ethyl-3-(3-dimethylaminopropyl) carbodiimide, hydrochloride), which is commercially available from Sigma-Aldrich (St. Louis, Mo.). Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as, N10-(3-sulfopropyl)-N-(3-carboxypropyl)-acridinium-9-carboxamide, otherwise known as CPSP-Acridinium Ester or N10-(3-sulfopropyl)-N-(3-sulfopropyl)-acridinium-9-carboxamide, otherwise known as SPSP-Acridinium Ester.

Alternatively, a second antibody that binds to analyte and that contains a detectable label can be added to the lysis mixture and used to detect the presence of the antibody-analyte complex. Any suitable detectable label can be used in this embodiment.

D. Illustrative Formats

The immunoassays of the invention can be conducted using any format known in the art, including, but not limited to, a sandwich format, a competitive inhibition format (including both forward or reverse competitive inhibition assays), or a fluorescence polarization format, and the like.

In immunoassays for the quantitative detection of an immunosuppressant, such as a preferred sandwich type format, at least two antibodies are employed to separate and quantify the drug in the lysis mixture. More specifically, the at least two antibodies bind to different parts of the drug, forming an immune complex which is referred to as a "sandwich". Generally, one or more antibodies can be used to capture (e.g., specifically bind) the analyte (e.g., the immunosuppressant) in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, it is preferred that both antibodies binding to the drug are not diminished by the binding of any other antibody in the assay to its respective binding site.

In other words, antibodies should be selected so that the one or more first antibodies brought into contact with a lysis mixture suspected of containing an immunosuppressant do not bind to all or part of the binding site recognized by the second or subsequent antibodies, thereby interfering with the ability of the one or more second or subsequent antibodies to bind to the drug. In a sandwich assay, the antibodies, and preferably, the at least one capture antibody, are used in molar excess amounts relative to the maximum amount of drug expected in the lysis mixture. For example, from about 5 μg/mL to about 1 mg/mL of antibody per mL of solid phase containing solution can be used.

In one embodiment, the at least one first capture antibody can be bound to a solid support which facilitates the separation of the first antibody-drug complex from the test sample. The solid support or "solid phase" used in the inventive immunoassay is not critical and can be selected by one skilled in the art. A solid phase or solid support, as used herein, refers to any material that is insoluble, or can be made insoluble by a subsequent reaction. Useful solid phases or solid supports are known to those in the art and include the walls of wells of a reaction tray, test tubes, polystyrene beads, magnetic beads, nitrocellulose strips, membranes, microparticles such as latex particles, sheep (or other animal) red blood cells, and Duracytes® (a registered trademark of Abbott Laboratories, Abbott Park, Ill.), which are red blood cells "fixed" by pyruvic aldehyde and formaldehyde, and others. Suitable methods for immobilizing peptides on solid phases include ionic, hydrophobic, covalent interactions and the like. The solid phase can be chosen for its intrinsic ability to attract and immobilize the capture agent. Alternatively, the solid phase can comprise an additional receptor that has the ability to attract and immobilize the capture agent. The additional receptor can include a charged substance that is oppositely charged with respect to the capture agent itself or to a charged substance conjugated to the capture agent. As yet another alternative, the receptor can be any specific binding partner which is immobilized upon (attached to) the solid phase and which has the ability to immobilize the capture agent through a specific binding reaction. The receptor molecule enables the indirect binding of the capture agent to a solid phase material before the performance of the assay or during the performance of the assay.

Any solid support known in the art can be used, including but not limited to, solid supports made out of polymeric materials in the forms of matrices, gels, wells, tubes or beads. The antibody (or antibodies) can be bound to the solid support by adsorption, by covalent bonding using a chemical coupling agent or by other means known in the art, provided that such binding does not interfere with the ability of the antibody to bind the drug. Moreover, if necessary, the solid support can be derivatized to allow reactivity with various functional groups on the antibody. Such derivatization typically involves the use of certain coupling agents such as, but not limited to, maleic anhydride, N-hydroxysuccinimide and 1-ethyl-3-(3-dimethylaminopropyl)carbodiimide.

It is within the scope of the present invention that the solid phase also can comprise any suitable porous material with sufficient porosity to allow access by detection antibodies and a suitable surface affinity to bind antigens. Microporous structure generally are preferred, but materials with gel structure in the hydrated state may be used as well. Such useful solid supports include but are not limited to nitrocellulose and nylon. It is contemplated that such porous solid supports described herein preferably are in the form of sheets of thickness from about 0.01 to 0.5 mm, preferably about 0.1 mm. The pore size may vary within wide limits, and preferably is from about 0.025 to 15 microns, especially from about 0.15 to 15 microns. The surface of such supports may be activated by chemical processes which cause covalent linkage of the antigen or antibody to the support. The irreversible binding of the antigen or antibody is obtained, however, in general, by adsorption on the porous material by hydrophobic forces.

After the lysis mixture suspected of containing or containing the immunosuppressant is brought into contact with the at least one first capture antibody, the resulting assay mixture is incubated to allow for the formation of a first capture antibody (or multiple antibody)-drug complex. The incubation can be carried out at any suitable pH, including a pH of from about 4.5 to about 10.0, at any suitable temperature, including from about 2° C. to about 45° C., and for a suitable time period from at least about one (1) minute to about eighteen (18) hours, preferably from about 4-20 minutes, most preferably from about 17-19 minutes.

After formation of the labeled complex, the amount of label in the complex can be quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. Once the amount of the label in the complex has been quantified, the concentration of drug in the test sample can be determined by use of a standard curve that has been generated, for example, using serial dilutions of immunosuppressant drug of known concentration. Other than using serial dilutions of the drug, the standard curve can be generated gravimetrically, by mass spectroscopy and by other techniques known in the art.

In a preferred forward competitive format, an aliquot of labeled drug, or analogue thereof, of a known concentration is used to compete with the drug present in a test sample for binding to the antibody. In a forward competition assay, an immobilized antibody can either be sequentially or simultaneously contacted with the test sample and a labeled drug or drug analogue thereof. The drug or drug analogue can be labeled with any suitable detectable label, including those detectable labels discussed above. In this assay, the capture antibody can be immobilized on to a solid support using the techniques discussed previously herein. Alternatively, the capture antibody can be coupled to an antibody, such as an antispecies antibody, that has been immobilized on to a solid support, such as a microparticle.

The labeled drug or drug analogue, the lysis mixture and the antibody are typically incubated under conditions similar to those described above in connection with the sandwich assay format. Two different types of antibody-drug complexes are then generated. Specifically, one of the antibody-drug complexes generated contains a detectable label while the other antibody-drug complex does not contain a detectable label. The antibody-drug complex can be, but does not have to be, separated from the remainder of the assay mixture prior to quantification of the detectable label. Regardless of whether the antibody-drug complex is separated from the remainder of the assay mixture, the amount of detectable label in the antibody-drug complex is then quantified. The concentration of drug in the test sample can then be determined by comparing the quantity of detectable label in the antibody-drug complex to a standard curve. The standard curve can be generated using serial dilutions of the drug of known concentration, by mass spectroscopy, gravimetrically and by other techniques known in the art.

The antibody-drug complex can be separated from the assay mixture by binding the antibody to a solid support, such as the solid supports discussed above in connection with the sandwich assay format, and then removing the remainder of the assay mixture from contact with the solid support.

In a reverse competition assay, an immobilized immunosuppressant drug or analogue thereof can either be sequentially or simultaneously contacted with a lysis mixture and at least one labeled antibody. The antibody can be labeled with any suitable detectable label, including those detectable labels discussed above. The drug or drug analogue can be bound to a solid support, such as the solid supports discussed above in connection with the sandwich assay format.

The immobilized drug or drug analogue, lysis mixture, and at least one labeled antibody are incubated under conditions similar to those described above in connection with the sandwich assay format. Two different types of antibody-drug complexes are then generated. Specifically, one of the antibody-drug complexes generated is immobilized and contains a detectable label while the other antibody-drug complex is not immobilized and contains a detectable label. The non-immobilized antibody-drug complex and the remainder of the assay mixture are removed from the presence of the immobilized antibody-drug complex through techniques known in the art, such as washing. Once the non-immobilized antibody-drug complex is removed, the amount of detectable label in the immobilized antibody-drug complex is then quantified. The concentration of drug in the test sample can then be determined by comparing the quantity of detectable label in the antibody-drug complex to a standard curve. The standard curve can be generated using serial dilutions of the drug of known concentration, by mass spectroscopy, gravimetrically and by other techniques known in the art.

In a fluorescence polarization assay, in one embodiment, an antibody or functionally active fragment thereof is first contacted with an unlabeled lysis mixture containing the immunosuppressant drug to form an unlabeled antibody-drug complex. The unlabeled antibody-drug complex is then contacted with a fluorescently labeled drug or analogue thereof. The labeled drug or drug analogue competes with any unlabeled drug in the assay mixture for binding to the antibody or functionally active fragment thereof. The amount of labeled antibody-drug complex formed is determined and the amount of drug in the test sample determined via use of a standard curve.

The use of scanning probe microscopy (SPM) for immunoassays also is a technology to which the immunoassay methods of the present invention are easily adaptable. In SPM, in particular in atomic force microscopy, a capture agent is affixed to a solid phase having a surface suitable for scanning. The capture agent can, for example, be adsorbed to a plastic or metal surface. Alternatively, the capture agent can be covalently attached to, e.g., derivatized plastic, metal, silicon, or glass according to methods known to those of ordinary skill in the art. Following attachment of the capture agent, the lysis mixture is contacted with the solid phase, and a scanning probe microscope is used to detect and quantify solid phase-affixed complexes. The use of SPM eliminates the need for labels which are typically employed in immunoassay systems. Such a system is described in U.S. Pat. No. 662,147, which is incorporated herein by reference.

Immunoassays according to the invention can also be carried out using a MicroElectroMechanical System (MEMS). MEMS are microscopic structures integrated onto silicon that combine mechanical, optical, and fluidic elements with electronics, allowing convenient detection of an analyte of interest. An exemplary MEMS device suitable for use in the invention is the Protiveris' multicantilever array. This array is based on chemo-mechanical actuation of specially designed silicon microcantilevers and subsequent optical detection of the microcantilever deflections. When coated on one side with a binding partner, a microcantilever will bend when it is exposed to a solution containing the complementary molecule. This bending is caused by the change in the surface energy due to the binding event. Optical detection of the degree of bending (deflection) allows measurement of the amount of complementary molecule bound to the microcantilever.

In other embodiments, immunoassays according to the invention are carried out using electrochemical detection. A basic procedure for electrochemical detection has been described by Heineman and coworkers. This entailed immobilization of a primary antibody (Ab, rat-anti mouse IgG), followed by exposure to a sequence of solutions containing the antigen (Ag, mouse IgG), the secondary antibody conjugated to an enzyme label (AP-Ab, rat anti mouse IgG and alkaline phosphatase), and p-aminophenyl phosphate (PAPP). The AP converts PAPP to p-aminophenol ($PAP_R$, the "R" is intended to distinguish the reduced form from the oxidized form, $PAP_O$, the quinoneimine), which is electrochemically reversible at potentials that do not interfere with reduction of oxygen and water at pH 9.0, where AP exhibits optimum activity. $PAP_R$ does not cause electrode fouling, unlike phenol whose precursor, phenylphosphate, is often used as the enzyme substrate. Although $PAP_R$ undergoes air and light oxidation, these are easily prevented on small scales and short time frames. Picomole detection limits for $PAP_R$ and femtogram detection limits for IgG achieved in micro-electrochemical immunoassays using PAPP volumes ranging from 20 µL to 360 µL have been reported previously. In capillary immunoassays with electrochemical detection, the lowest detection limit reported thus far is 3000 molecules of mouse IgG using a volume of 70 µL and a 30 minute or 25 minute assay time.

Various electrochemical detection systems are described in U.S. Pat. No. 7,045,364 (issued May 16, 2006; incorporated herein by reference), U.S. Pat. No. 7,045,310 (issued May 16, 2006; incorporated herein by reference), U.S. Pat. No. 6,887,714 (issued May 3, 2005; incorporated herein by reference), U.S. Pat. No. 6,682,648 (issued Jan. 27, 2004; incorporated herein by reference); U.S. Pat. No. 6,670,115 (issued Dec. 30, 2003; incorporated herein by reference). In particular embodiments, useful, for example, for simultaneously assaying multiple analytes in one test sample, the solid phase can include a plurality different capture agents. Thus, for example, the solid phase can have affixed thereon a plurality of antibodies, wherein each is intended to test for the presence of different analytes in the sample. In an exemplary embodiment, the solid phase can consist of a plurality of different regions on a surface, wherein each region has a particular antibody affixed therein.

Multiplex formats can, but need not, employ a plurality of labels, wherein each label is used for the detection of a particular analyte. For example, multiple, different analytes can be detected without using a plurality of labels where a plurality of capture agents, such as antibodies, are affixed to the solid phase at different known locations, based on specificity. Because the specificity of the capture agent at each location is known, the detection of a signal at a particular location can be associated with the presence of analyte bound at that location. Examples of this format include microfluidic devices and capillary arrays, containing different capture agents at different locations along a channel or capillary, respectively, and microarrays, which typically contain different capture agents arranged in a matrix of spots ("target elements") on a surface of a solid support. In particular embodiments, each different capture agent can be affixed to a different electrode, which can, for example, be formed on a surface of a solid support, in a channel of a microfluidic device, or in a capillary.

III. Test Kits

The invention also provides test kits for assaying test samples for an analyte. Test kits according to the invention include one or more reagents useful for practicing one or more immunoassays according to the invention. A test kit generally includes a package with one or more containers holding the reagents, as one or more separate compositions or, optionally, as admixture where the compatibility of the reagents will allow. The test kit can also include other material(s), which may be desirable from a user standpoint, such as a buffer(s), a diluent(s), a standard(s), and/or any other material useful in sample processing, washing, or conducting any other step of the assay.

In certain embodiments, test kits of the invention can include: (a) at least one antibody or other ligand (e.g., binding protein) capable of binding specifically to at least one analyte; and (b) one or more proteases as described herein. Illustrative proteases include, but are not limited to proteinase K, subtilisin, dispase, thermolysin, trypsin, ficin, bromelain, and combinations thereof. The kit optionally further comprises (c) a lysis reagent comprising: a glycol selected from the group consisting of ethylene glycol, propylene glycol, and an analog thereof; and at least one alcohol as described herein (e.g., an alcohol having five or fewer carbons), or the components of such a lysis reagent. In illustrative embodiments, useful for carrying out immunoassays for immunosuppressant drugs, the antibody can be specific for rapamycin (sirolimus), tacrolimus, everolimus, temsorolimus, zotarolimus, cyclosporine, or analogs of any of these compounds.

In certain embodiments, the lysis reagent includes methanol, ethanol, propanol, or a mixture of any of these alcohols. In illustrative embodiments, the ratio of glycol to alcohol is in the range of about 4:1 to about 1:4, more particularly, in the range of about 4:1 to about 1:2.

If desired, the test kit can additionally include a control composition that includes the immunosuppressant drug being assayed.

In particular embodiments, test kits according to the invention can include one or more detergents and/or agents that release the analyte from one or more binding proteins in the test sample. Suitable detergents or detergent combinations include non-ionic detergents, such as saponin, as described above. Suitable releasing agents include agents that compete with the analyte for binding to one or more binding proteins, as described above. Any detergents or proteases provided in kits of the invention should be provided in a manner that facilitates the production of a lysis mixture containing the components in suitable concentration, as described above.

Kits according to the invention can include a solid phase and a capture agent that is affixed to the solid phase or that becomes solid phase-affixed during the assay. In exemplary embodiments, the solid phase includes one or more microparticles or electrodes. Where such kits are to be employed for conducting sandwich immunoassays, the kits can additionally include a labeled detection agent. In certain embodiments, the test kit includes at least one direct label, such as acridinium-9-carboxamide. Test kits according to the invention can also include at least one indirect label. If the label employed generally requires an indicator reagent to produce a detectable signal, the test kit preferably includes one or more suitable indicator reagents.

Test kits according to the invention preferably include instructions for carrying out one or more of the immunoassays of the invention. Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, for example, computer media including, but are not limited to, electronic storage media (e.g., magnetic discs, tapes, cartridges, chips), optical media (e.g., CD ROM), and the like. As used herein, the term "instructions" can include the address of an internet site that provides the instructions.

Of course, it goes without saying that any of the exemplary formats herein, and any assay or kit according to the invention can be adapted or optimized for use in automated and semi-automated systems (including those in which there is a solid phase comprising a microparticle), as described, e.g., in U.S. Pat. Nos. 5,089,424 and 5,006,309, and as, e.g., commercially marketed by Abbott Laboratories (Abbott Park, Ill.) including but not limited to Abbott Laboratories' ARCHITECT®, AxSYM®, IMX®, ABBOTT PRISM®, and Quantum II platforms, as well as other platforms.

Additionally, the assays and kits of the present invention optionally can be adapted or optimized for point of care assay systems, including Abbott Laboratories' Point of Care (i-STAT™) electrochemical immunoassay system. Immunosensors and methods of manufacturing and operating them in single-use test devices are described, for example in U.S. Pat. No. 5,063,081 and published U.S. Patent Applications 20030170881, 20040018577, 20050054078, and 20060160164 (incorporated by reference herein for their teachings regarding same).

EXAMPLES

The following examples are offered to illustrate, but not to limit, the claimed invention.

Example 1

Comparison of Proteases

The following proteases were tested in assay mixtures as described herein, comprised of either lysed whole blood diluent (i.e., "Calibrator Diluent"), or whole, unlysed fresh specimen blood (i.e., patient specimens, or "Fresh Blood"): alpha-chymotrypsin (CH); PE=pepsin (PE); proteinase K (PK), and thermolysin (TH).

The ARCHITECT® Sirolimus assay (homogeneous concept-phase assay subsequently marketed by Abbott Laboratories, Abbott Park, Ill.) was employed for these studies. Calibrated sirolimus standards were prepared in a lysed whole blood diluent (IMx® Tacrolimus II Blood Diluent, Abbott Laboratories, Abbott Park, Ill.), namely CAL A and F CAL, comprising 0 and 30 ng/mL sirolimus (Wyeth-Pharma GmbH, Münster, Germany), respectively.

In the ARCHITECT® Sirolimus assay, the amount of light (or signal) produced by a sample (typically following assay) is measured as relative light units (RLUs). RLU is the designation for the unit of optical measurement employed on the ARCHITECT® system, as well as in other instruments. The term RLU comes from the relation of the photon counting to a certain amount of signal-producing standard, such as acridinium. Each optics module is calibrated with a set of standards (e.g., acridinium standards). When the chemiluminescent reaction occurs, light is emitted and the photons are measured over a period of time (e.g., a 3 second time period). The photomultiplier tube (PMT) converts the photons counted to digital signal, which is then sent to a circuit board for processing. The optics circuit board converts the digital signal from the PMT to an analog signal that is proportional to the photons counted, which is in turn proportional to the amount of signal producing molecule (e.g., acridinium) present. This analog signal is then further processed to produce an RLU value. This relationship was established to produce a standard for calibration of the optics module, where the different standards have RLU values assigned to them. Thus, while the RLU unit itself is arbitrary, it is proportional (i.e., relative) to a certain amount of standard (e.g., acridinium).

In these studies, "bias" was calculated as the % difference in signal (RLU) from the Fresh Blood samples spiked with a sirolimus concentration (e.g., 30 ng/mL or 0 ng/mL) (i.e., "Fresh Blood Samples") equivalent to the sirolimus concentration of the calibrators prepared with Assay Diluent (i.e., "Assay Diluent Samples"). In other words, bias was calculated as the difference in signal exhibited by fresh blood specimen calibrators (e.g., non-lysed) when compared to lysed whole blood calibrators (freeze-thawed, approx 80% whole blood, >1 month old). Such a value presumably represents the bias that would be seen in patient specimens at similar concentrations, and accounts for the large (e.g. >50%) shift in patient specimens observed when they are stored at room temperature and assayed by a homogeneous sirolimus assay (e.g., commercial Abbott ARCHITECT® Sirolimus assay) over time.

Although it seems that all of the proteases had some affect on the bias, clearly Proteinase K and Thermolysin had the largest impact (data not shown). Thermolysin increased the F CAL RLU values in the Assay Diluent Samples and the Fresh Blood Samples, and at 500 µg/mL (amount in the pre-treated homogeneous specimen/sample, before being sampled by the ARCHITECT® for measurement of free Sirolimus), the F CAL bias is reduced to about 30%. The CAL A at the 500 µg/mL (amount in the pre-treated homogeneous specimen/sample), however, moved in the opposite direction, creating a −24% bias.

Proteinase K also increased the F CAL RLU values in the Assay Diluent Samples, however, it reduced the RLU values in the Fresh Blood Samples. The CAL A bias was a little worse at 50 µg/mL (~15%), however, at 500 µg/mL the bias improved to 6-7%.

Proteases thus have an affect on the Fresh Blood Samples vs. Assay Diluent Samples bias. The bias observed was dependent on the concentration of Sirolimus. The lower the concentration of Sirolimus, the less bias was observed, and essentially no bias was observed at the CAL A (0 ng/mL) level. This finding would be unexpected if the problem was an interferant or non-specific binding. Because the assay was done in a competitive format, the CAL A has the highest RLU signal. It is unusual to have no bias at the highest level of signal, but then to have greater bias with lower signal (e.g. higher Sirolimus levels), unless there is a difference in affinity (e.g. the FKBP12 affinity for Sirolimus in fresh whole blood vs. in stored lysed whole blood). If the mechanism is the clipping of protease FKPB12, then this would explain the difficulty in finding a non-specific agent (e.g., HSA or Lipoprotein binder) to affect the bias in a Sirolimus-dependent manner. A change in the binding affinity of FKBP12 would be very difficult to match by other means. Taken together, this data, i.e., the Fresh Blood Samples stability data and the Sirolimus concentration dependency support proteolytic cleavage as the mechanism for the bias.

Example 2

Comparison of Proteinase K or Thermolysin in Sirolimus Assay

In this experiment, Sirolimus calibrators TA and FA were made in lysed (by freeze-thaw) whole blood with preservatives and which had been stored at 4° C. for greater than one month (i.e., "Calibrator Diluent"). These so-called Assay Diluent Samples, TA and FA, contained 0 and 30 ng/mL Sirolimus, respectively. Fresh whole unlysed fresh specimen blood (i.e., patient specimens, or "Fresh Blood") calibrators WA and WF (so-called Fresh Blood Samples) contained 0 and 30 ng/mL Sirolimus, respectively.

Assay Diluent Samples and Fresh Blood Samples were treated with increasing levels of either Proteinase K or Thermolysin at concentrations of 50, 250, or 500 µg/mL. Controls were samples identical to Assay Diluent Samples and Fresh Blood Samples in all other respects, but which were left untreated. Protease was added to all samples in a 5% propylene glycol/5% ethanol solution at a volume ratio of 2 parts organic solution:1 part sample (i.e., samples being the Assay Diluent Sample, Fresh Blood Sample, or counterpart controls). Samples were then vortexed and placed immediately on the ARCHITECT® instrument for testing in a delayed 1-step competitive format.

Key to abbreviations in Tables 1-3 below:
A: calibrator A, 0 ng/mL
F: calibrator F, 30 ng/mL
T: stored lysed whole blood diluent
W: fresh whole blood
PK (number): Proteinase K added at 50, 250 or 500 µg/mL concentrations
TH (number): Thermolysin added at 50, 250 or 500 µg/mL concentrations

TABLE 1

Controls

| Samples | RLUs | % Difference |
|---|---|---|
| TA | 747610 | |
| TF | 54112 | |
| WA | 675721 | −9.6 |
| WF | 100334 | 85.4 |

TABLE 2

Proteinase K-containing Samples

| Samples | RLUs | % Difference |
|---|---|---|
| PK50TA | 831449 | |
| PK50TF | 64774 | |
| PK50WA | 708890 | −14.7 |
| PK50WF | 111464 | 72.1 |
| PK250TA | 881927 | |
| PK250TF | 77396 | |
| PK250WA | 749423 | −15 |
| PK250WF | 85159.5 | 10 |
| PK500TA | 862392 | |
| PK500TF | 80400 | |
| PK500WA | 807796 | −6.3 |
| PK500WF | 85000 | 5.7 |

TABLE 3

Thermolysin-containing Samples

| Samples | RLUs | % Difference |
|---|---|---|
| TH50TA | 751667 | |
| TH50TF | 67714 | |
| TH50WA | 679040 | −9.7 |
| TH50WF | 105856 | 56.3 |
| TH250TA | 776427 | |
| TH250TF | 67910 | |
| TH250WA | 663988 | −14.5 |
| TH250WF | 110980 | 63.4 |
| TH500TA | 901042 | |
| TH500TF | 89824 | |
| TH500WA | 690567 | −23.4 |
| TH500WF | 116174.5 | 29.3 |

As can be seen from Table 1, there is a −10% bias between fresh blood calibrators (Fresh Blood Samples WA and WF) and stored lysed blood calibrators (Assay Diluent Samples TA and TF) in the signal generated with 0 ng/mL Sirolimus present. As can be seen from Table 2, At 500 µg/mL of Proteinase K, this bias is reduced to about −6%.

There is an 85% bias between fresh blood calibrators (WA and WF) and stored lysed blood calibrators (Assay Diluent Samples TA and TF) in the signal generated with 30 ng/mL Sirolimus present (Table 1). At 500 µg/mL of Proteinase K, this bias is reduced to about 6% (Table 2), and at 500 µg/mL of Thermolysin, this bias is reduced to about 29% (Table 3).

Based on the foregoing data, proteases have a direct impact on the bias in signal generated between fresh blood and lysed whole blood calibrators in a Sirolimus assay, competitive format, which in the case of the F calibrator indicates a normalization of the measurable concentrations of free Sirolimus.

It is understood that the examples and embodiments described herein are for illustrative purposes only and that various modifications or changes in light thereof will be suggested to persons skilled in the art and are to be included within the spirit and purview of this application and scope of the appended claims.

The commonly owned, co-pending application U.S. Provisional Application Ser. No. 60/878,017 filed on Dec. 29, 2006 is explicitly incorporated by reference in its entirety for its teachings regarding a non-denaturing lysis reagent for use with capture-in-solution immunoassay.

The commonly owned, co-pending application U.S. Non-provisional application Ser. No. 11/618,495 filed on Dec. 29, 2006 is explicitly incorporated by reference in its entirety for its teachings regarding a non-denaturing lysis reagent.

The commonly owned, co-pending application U.S. Provisional Application Ser. No. 60/882,863 filed on Dec. 29, 2006 is explicitly incorporated by reference in its entirety for its teachings regarding an improved assay for immunosuppressant drugs.

The commonly owned, co-pending application U.S. Non-provisional application Ser. No. 11/490,624 filed on Jul. 21, 2006 is explicitly incorporated by reference in its entirety for its teachings regarding an extractive reagent composition.

In addition, all other publications, patents, and patent applications cited herein are hereby incorporated by reference in their entirety for all purposes.

What is claimed is:

1. A method for assessing the concentration of an immunosuppressant drug in a test sample, the method comprising:
   contacting a test sample with an assay reagent to produce an assay mixture compatible for use in an immunoassay without subsequent extraction steps, wherein the assay reagent comprises:
      a lysis reagent, wherein said lysis reagent comprises a glycol selected from the group consisting of ethylene glycol, propylene glycol, and an analog thereof; and at least one alcohol having five or fewer carbons; and
      a protease that has proteolytic activity for an intracellular ligand that binds said immunosuppressant drug; and
   assaying the lysis mixture for an immunosuppressant drug, wherein the method does not comprise contacting the test sample with a detergent.

2. The method of claim 1, wherein the assay mixture is a homogeneous mixture.

3. The method of claim 1, wherein the assay comprises an immunoassay.

4. The method of claim 1, wherein the immunosuppressant drug is selected from the group consisting of sirolimus, tacrolimus, everolimus, zotarolimus, cyclosporine, and analogs of any of these compounds.

5. The method of claim 1, wherein the test sample comprises a human blood sample.

6. The method of claim 1, wherein the test sample comprises whole blood or a blood fraction.

7. The method of claim 1, wherein the method does not comprise centrifuging the lysis mixture.

8. The method of claim 1, wherein said protease is selected from the group consisting of a serine protease, a metalloprotease, a cysteine protease, an aspartic acid protease, and a glutamic acid protease.

9. The method of claim 1, wherein said protease is selected from the group consisting of pepsin, proteinase K, thermolysin, dispase, trypsin, and chymotrypsin.

10. A method for assessing the concentration of an immunosuppressant drug in a test sample, the method comprising:
contacting a test sample with an assay reagent to produce an assay mixture compatible for use in an immunoassay without subsequent extraction steps, wherein the assay reagent comprises:
a lysis reagent; and
a protease that has proteolytic activity for an intracellular ligand that binds said immunosuppressant drug; and
assaying the lysis mixture for an immunosuppressant drug, wherein said protease is selected from the group consisting of a serine protease, a metalloprotease, a cysteine protease, an aspartic acid protease, and a glutamic acid protease, wherein said lysis reagent comprises a glycol selected from the group consisting of ethylene glycol, propylene glycol, and an analog thereof; and at least one alcohol having five or fewer carbons.

11. The method of claim 10, wherein the alcohol is selected from the group consisting of methanol, ethanol, and propanol.

12. The method of claim 11, wherein the ratio of glycol to alcohol is in the range of about 4:1 to about 1:4.

13. The method of claim 11, wherein the ratio of glycol to alcohol is in the range of about 4:1 to about 1:2.

14. The method of claim 11, wherein the test sample is added to the lysis reagent at a ratio in the range of about 2:1 to about 1:10.

15. The method of claim 11, wherein the test sample is added to the lysis reagent at a ratio in the range of about 2:1 to about 1:2.

16. The method of claim 11, wherein the method does not comprise centrifuging the sample.

17. The method of claim 1, wherein said assay reagent further comprises a competitor that competes with the immunosuppressant drug for binding by the intracellular ligand, but is not cross-reactive with a capture agent in the assay detection system.

18. The method of claim 1, wherein the competitor comprises a different, but structurally similar, immunosuppressant drug.

19. A method for preparing a test sample for use in an assay for detecting an immunosuppressant drug bound by an intracellular ligand, the method comprising contacting said test sample with an assay reagent comprising:
a lysis reagent, wherein said lysis reagent comprises a glycol selected from the group consisting of ethylene glycol, propylene glycol, and an analog thereof; and at least one alcohol having five or fewer carbons; and
a protease that has proteolytic activity for said intracellular ligand that binds said immunosuppressant drug;
to form a mixture compatible for use in an immunoassay without subsequent extraction steps, wherein a detergent is not used to lyse or solubilize the test sample.

20. The method of claim 19, wherein said test sample is whole blood or a blood fraction.

21. The method of claim 19, wherein said test sample comprises human blood.

22. The method of claim 19, wherein said test sample comprises human blood drawn from a subject under treatment for an autoimmune disease, or having a heterologous graft or organ transplant.

23. The method of claim 19, wherein said protease is selected from the group consisting of a serine protease, a metalloprotease, a cysteine protease, an aspartic acid protease, and a glutamic acid protease.

24. The method of claim 23, wherein said protease is selected from the group consisting of pepsin, proteinase K, thermolysin, dispase, trypsin, and chymotrypsin.

25. The method of claim 19, wherein the alcohol is selected from the group consisting of methanol, ethanol, and propanol.

26. The method of claim 19, wherein the ratio of glycol to alcohol is in the range of about 4:1 to about 1:4.

27. The method of claim 19, wherein the ratio of glycol to alcohol is in the range of about 4:1 to about 1:2.

28. The method of claim 19, wherein the test sample is added to the lysis reagent at a ratio in the range of about 2:1 to about 1:10.

29. The method of claim 19, wherein the test sample is added to the lysis reagent at a ratio in the range of about 2:1 to about 1:2.

30. The method of claim 19, wherein the method does not comprise centrifuging the sample.

31. The method of claim 19, wherein said assay reagent further comprises a competitor that competes with the immunosuppressant drug for binding by the intracellular ligand, but is not cross-reactive with the immunosuppressant drug in the assay detection system.

32. The method of claim 19, wherein said intracellular ligand is an immunophilin ligand.

33. The method of claim 31, wherein the competitor comprises a structurally similar analogue of the immunosuppressant drug.

34. The method of claim 19, wherein said intracellular ligand binds an immunosuppressant drug selected from the group consisting of tacrolimus, everolimus, zotarolimus, cyclosporine, and analogs of any of these compounds.

35. A test kit for use in the method of claim 1, comprising:
(a) at least one antibody or protein capable of binding specifically to at least one immunosuppressant drug selected from the group consisting of sirolimus, tacrolimus, everolimus, zotarolimus, cyclosporine, and an analog of any of these compounds; and
(b) an assay reagent comprising:
a non-detergent lysing reagent, wherein said lysis reagent comprises a glycol selected from the group consisting of ethylene glycol, propylene glycol, and an analog thereof; and at least one alcohol having five or fewer carbons; and
a protease that degrades an immunophilin ligand.

36. The kit of claim 35, wherein said protease is selected from the group consisting of pepsin, proteinase K, thermolysin, dispase, trypsin, and chymotrypsin.

37. The test kit of claim 35, additionally comprising a control composition comprising the at least one immunosuppressant drug of (a).

38. The test kit of claim 35, wherein the alcohol is selected from the group consisting of methanol, ethanol, and propanol.

39. The test kit of claim 35, wherein the ratio of glycol to alcohol is in the range of about 4:1 to about 1:4.

40. The test kit of claim 35, wherein the ratio of glycol to alcohol is in the range of about 4:1 to about 1:2.

41. The test kit of claim 35, wherein the kit further comprises a competitor that competes with the immunosuppressant drug for binding by an intracellular ligand, but is not cross-reactive with the immunosuppressant drug in the assay detection system.

42. The test kit of claim 41, wherein said competitor is provided in the assay reagent.

43. The test kit of claim 35, wherein said intracellular ligand is an immunophilin ligand.

44. The test kit claim 41, wherein the competitor comprises an analogue that is different from, but structurally similar to, the immunosuppressant drug being assayed.

* * * * *